United States Patent
Jarisch

(10) Patent No.: US 8,660,328 B2
(45) Date of Patent: Feb. 25, 2014

(54) HIGH EFFICIENCY COMPUTER TOMOGRAPHY

(76) Inventor: Wolfram R. Jarisch, Potomac, MD (US)

(*) Notice: Subject to any disclaimer, the term of this patent is extended or adjusted under 35 U.S.C. 154(b) by 745 days.

(21) Appl. No.: 12/493,989

(22) Filed: Jun. 29, 2009

(65) Prior Publication Data

US 2009/0324047 A1 Dec. 31, 2009

Related U.S. Application Data

(60) Provisional application No. 61/129,459, filed on Jun. 27, 2008.

(51) Int. Cl.
*G06K 9/00* (2006.01)
*G06K 9/40* (2006.01)

(52) U.S. Cl.
USPC .................................. 382/131; 382/254

(58) Field of Classification Search
None
See application file for complete search history.

(56) References Cited

U.S. PATENT DOCUMENTS

| | | | |
|---|---|---|---|
| 4,593,355 A * | 6/1986 | Chase | 382/131 |
| 5,566,341 A | 10/1996 | Roberson et al. | |
| 6,018,562 A | 1/2000 | Willson | |
| 6,110,113 A | 8/2000 | Banjamin et al. | |
| 6,332,035 B1 | 12/2001 | Basu et al. | |
| 6,345,113 B1 | 2/2002 | Crawford et al. | |
| 6,859,564 B2 | 2/2005 | Caron | |
| 7,825,667 B2 * | 11/2010 | Fang et al. | 324/637 |
| 7,978,896 B2 * | 7/2011 | Kimura | 382/131 |
| 2006/0072801 A1 * | 4/2006 | Bernard Deman et al. | 382/131 |
| 2006/0104410 A1 | 5/2006 | Sauer et al. | |
| 2007/0237295 A1 | 10/2007 | Gundel | |
| 2007/0239403 A1 * | 10/2007 | Hornbostel | 702/191 |

(Continued)

FOREIGN PATENT DOCUMENTS

| | | |
|---|---|---|
| CN | 101023867 A | 8/2007 |
| JP | 2006-105975 | 4/2006 |

(Continued)

OTHER PUBLICATIONS

"X-ray computed tomography" [online], 2012, retrieved from the internet: < URL: http://en.wikipedia.org/wiki/X-ray_computed_tomography >, pp. 1-20.*

(Continued)

*Primary Examiner* — Bhavesh Mehta
*Assistant Examiner* — David F Dunphy
(74) *Attorney, Agent, or Firm* — Venable LLP; Michael A. Sartori; Todd R. Farnsworth

(57) ABSTRACT

A system comprising: one or more transmitters to transmit an excitation energy into an object under observation; one or more detectors to generate projection space data encoding an energy received by the one or more detectors in response to the transmitted excitation energy into the object under observation; a controller to control the one or more transmitters to transmit the excitation energy and the one or more detectors to generate the projection space data; and an image reconstructor to receive the projection space data and to process the projection space data by: computing a first quantity characterizing a difference between the projection space data and predicted projection data; computing a second quantity corresponding to at least one impulse response, each impulse response corresponding to a reference voxel of unit-intensity; computing an update value using the first quantity and an inverted function of the second quantity; and reconstructing an object space image representing the object under observation using the update value.

32 Claims, 7 Drawing Sheets

(56) References Cited

U.S. PATENT DOCUMENTS

| | | |
|---|---|---|
| 2008/0118020 A1 | 5/2008 | Thibault et al. |
| 2009/0060121 A1 | 3/2009 | Ziegler et al. |
| 2009/0262997 A1 | 10/2009 | Zou et al. |
| 2009/0279768 A1 | 11/2009 | Nishikawa |
| 2009/0324047 A1 | 12/2009 | Jarisch |
| 2010/0070836 A1 | 3/2010 | Wegener et al. |

FOREIGN PATENT DOCUMENTS

| | | |
|---|---|---|
| WO | WO-2007/120300 A2 | 10/2007 |
| WO | WO-2009/158714 A1 | 12/2009 |
| WO | WO-2009-158718 A1 | 12/2009 |

OTHER PUBLICATIONS http://en.wikipedia.org/wiki/Wiener_filter, last accessed Oct. 16, 2009.

Box, G.E.P. et al., "An analysis of transformations," Journal of the Royal Statistical Society, Series B, vol. 26, pp. 211-246, 1964.

Wiener, N., Extrapolation, Interpolation, and Smoothing of Stationary Time Series, pp. 81-91, 94-99, New York, Wiley, 1949.

Kolehmainen, V. et al., "Structure-From-Motion Without Correspondence From Tomographic Projections by Bayesian Inversion Theory," IEEE Trans. Medical Imaging, ITMID4, vol. 26, No. 2, pp. 238-248, Feb. 2007.

Sage, A.P. et al., "Estimation Theory with Applications to Communications and Control, New York, McGraw-Hill," pp. 262, 1971.

Wang, J. et al., "Multiscale Penalized Weighted Least-Squares Sinogram Restoration for Low-Dose X-Ray Computed Tomography," IEEE Trans. on Biomed. Eng., vol. BME-55, No. 3, pp. 1022-1031, Mar. 2008.

Trachtenberg, S., et al., "Structure of the Cytoskeleton of Spiroplasma Melliferum BC3 and its Interactions with the Cell Membrane," J. Mol. Biol., vol. 378, pp. 776-787, 2008.

Jarisch, et al., "Statistical Modeling of Fetal Heart Rate Variability," IEEE Trans. on Biomed. Eng., vol. BME-27, No. 10, pp. 582-589, Oct. 1980.

Hansis, E. et al., "Evaluation of Iterative Sparse Object Reconstruction From Few Projections for 3-D Rotational Coronary Angiography," IEEE Trans. Med. Imaging, vol. 27, No. 11, ITMID4, pp. 1548-1555, Nov. 2008.

Wood & Morf, "A Fast Implementation of a Minimum Variance Estimator for Computerized Tomography Image Reconstruction," IEEE, Trans. on Biomed. Eng., vol. BME-28, No. 2, pp. 56-68, 1981.

Jarisch, W.R., "Determination of Material Properties by Limited Scan X-Ray Tomography," Technical Report, USAF AFWAL-TR-81-4050, Wright-Patterson Air Force Base, Ohio, pp. 2, 4, 5-7, 9, 13-14, 17, 20, 22, 24, 26-28, 30-31, 120-124, Sep. 1981.

Larimore, "Orthogonal Projection Techniques and Optimal Estimation of Linear Dynamic Processes," Thesis, George Washington University, pp. 17-18, 21-22, 30-37, 41-49, and 60-63, Jun. 1970.

Fessler, J. et al., "Object-Based 3-D Reconstruction of Arterial Trees from Magnetic Resonance Angiograms," IEEE Trans. on Medical Imaging, vol. 10, No. 1, pp. 25-39, Mar. 1991.

Fessler, J. et al., "Conjugate-Gradient Preconditioning Methods for Shift-Variant PET Image Reconstruction," IEEE Trans. on Image Processing, vol. 8, No. 5, pp. 688-699, May 1999.

Ahlen, A. et al., "Wiener Filter Design Using Polynomial Equations," IEEE Trans. on Signal Processing, vol. 39, No. 11, pp. 2387-2399, Nov. 1991.

Goldstein, J.S. et al., "A Multistage Representation of the Wiener Filter Based on Orthogonal Projections," IEEE Trans. on Information Theory, vol. 44, No. 7, pp. 2943-2959, Nov. 1998.

Dohnalkova, A. et al., "CryoTEM Tomography Provides a New Perspective to the Bacterial-Mineral Association in Biogeochemistry Studies," Proceedings of the Asia-Pacific Congress on Electron Tomography, University of Queensland, Brisbane, Australia, Jan. 1-Feb. 4, 2009.

Jarisch, W.R. et al., "Computed Tomographic (CT) Reconstruction of the Average Propagator from Diffusion Weighted MR Data," ISMRM, Honolulu, Hawaii, Apr. 18-24, 2009.

Jarisch, W.R., "HECT—High Efficiency Computed Tomography, A Powerful New Technique for Quantitative Tomography," Microscopy and Microanalysis, Albuquerque, NM, Late Braking Poster #16, Aug. 3-7, 2008.

Jarisch, W.R. et al., "High Efficiency CT (HECT) for Automated Alignment and Contrast Calibration of Projections in Quantitative TEM Tomography," Microscopy and Microanalysis Conference, Richmond, VA, Jul. 26-30, 2009.

Sternad, M., Lindborn, L., Ahlen, A., "Wiener design of adaptation algorithms with time-invariant gains," IEEE Trans. Signal Proc., vol. 50, No. 8, pp. 1895-1907, 2002.

Box, G.E.P., Jenkins, G.M., Time Series Analysis: Forecasting and Control, San Francisco, CA: Holden-Day, pp. 94, 1976.

Brandt, S.S. et al., "Structure-From-Motion Without Correspondence From Tomographic Projections by Bayesian Inversion Theory," IEEE Trans. Medical Imaging, ITMID4, vol. 26, No. 2, pp. 238-248, Feb. 2007.

Larimore, W. "Orthogonal Projection Techniques and Optimal Estimation of Linear Dynamic Processes," Thesis, George Washington University, pp. 17-18, 21-22, 30-37, 41-49, and 60-63, Jun. 1970.

X. Pan, "Tomographic Image Reconstruction," presented at 41st Annual Meeting of the American Association of Physicists in Medicine. Nashville, TN, 1999.

Zosso, M. Bach Cuadra, and J.-P. Thiran, "Direct fourier tomographic reconstruction image-to-image filter," Insight Journal, Jul.-Dec. 2007.

Pan, T-S. et al., "Acceleration and Filtering in the Generalized Landweber Iteration Using a Variable Shaping Matrix,"IEEE Trans. on Medical Engineering, vol. 12, No. 2, pp. 278-286, Jun. 1993.

Office Action in Japanese Patent Application No. 2011-516784 dated Jun. 11, 2013.

Office Action in U.S. Appl. No. 12/838,205 dated Dec. 3, 2012.

Notice of Allowance in U.S. Appl. No. 12/838,205 dated May 15, 2013.

Office Action in Chinese Patent Application No. 200980123522.8 dated May 28, 2013.

Extended European Search Report in European Patent Application No. 09771249.1 dated Sep. 4, 2012.

Office Action in Chinese Patent Application No. 200980123522.8 dated Oct. 8, 2012.

International Search Report and Written Opinion in International Application No. PCT/US11/44005 dated Nov. 18, 2011.

International Search Report and Written Opinion in International Application No. PCT/US09/49102 dated Aug. 19, 2009.

International Preliminary Report on Patentability in PCT/US09/49102 dated Oct. 28, 2010.

\* cited by examiner

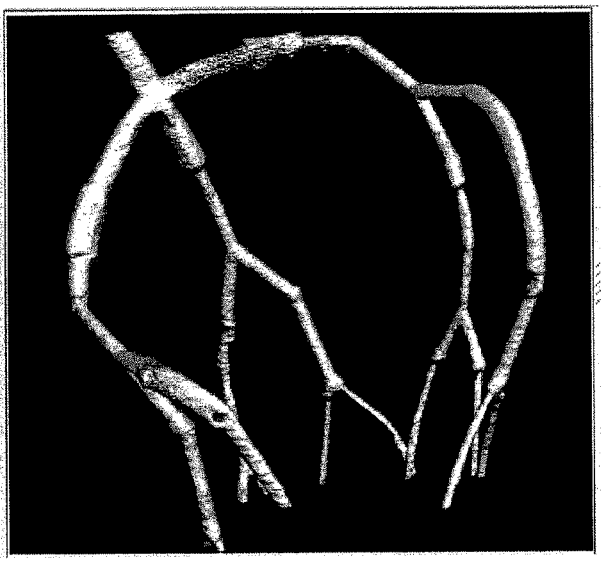
FIG. 7A          FIG. 7B

HIGH EFFICIENCY COMPUTER TOMOGRAPHY

CROSS-REFERENCE OF RELATED APPLICATION

This application claims priority to U.S. Provisional Application No. 61/129,459 filed Jun. 27, 2008, the entire contents of which are hereby incorporated by reference.

FIELD OF INVENTION

The current invention relates to the field of image reconstruction.

BACKGROUND OF INVENTION

Tomography, the computation (estimation) of a density in a region in a n-dimensional space based on m-dimensional projections of that region (represented as pixels; usually $0<m<n$), falls into two major categories: filtered back-projection (FBP) and iterative reconstruction (IR), which is also known as a variant of the Algebraic Reconstruction Technique (ART). Both FBP and conventional IR techniques have specific deficiencies, especially in modern settings that often require $10^6$-$10^{10}$ image elements (i.e., voxels) to be computed when one projection often contains anywhere from 2000 pixels (one-dimensional) up to 2000×2000 pixels (two-dimensional).

Major deficiencies associated with FBP include the need for a large number of projections to achieve limited quantitative accuracy. The number of projections is typically counted in the hundreds but the projections are not used as efficiently as they might. For example, computed density estimates may be negative while it is known that physical intensities cannot be negative. The limited quantitative accuracy may sometimes be improved by subsequent iterative refinement. Other deficiencies associated with the FBP include the inability to change data-weights depending on voxel location, as discussed in Wood, S. L., Morf, M., *A fast implementation of a minimum variance estimator for computerized tomography image reconstruction*, IEEE, Trans. on Biomed. Eng., Vol. BME-28, No. 2, pp. 56-68, 1981 (hereinafter Wood) and the inability to effectively consider a variety of constraints.

The strength of the FBP method include its computation speed as it typically relies on the fast Fourier transformation, central slice theorem, and possibly the use of suitable and pre-computed filters.

Alternative techniques to the FBP and conventional IR techniques use matrix operations and may be applicable for "small" problems in which the number of volume or picture elements (voxels or pixels) is in the few-thousands. For typical tomographic reconstruction settings, however, the computational burden cannot be handled in the foreseeable future by these matrix-based techniques. This is because the number of computer operations scales as a power of N. For example, in a 3-D case the operations count could scale faster than $N^5$ (where N is the number of pixels of a side of a reconstruction cube, representing the region of interest), as discussed in Wood and U.S. Pat. No. 6,332,035, Dec. 18, 2001.

The benefits of IR techniques include their ability to account for constraints, especially the ability to assure density estimates to be non-negative. Assuring non-negative density estimates may lead to a significant image contrast improvement and better quantitative results.

The deficiencies associated with conventional IR techniques include the need to solve repeatedly an inversion operation as well as a forward projection operation in order to obtain corrections terms for subsequent iterations. The concomitant need for many recursive pairings of these operations usually make the IR techniques slow and, depending on particular implementations, unstable.

Because these conventional IR techniques use various (iterative) optimization methods, their rate of convergence to the solution depends on how well a particular technique accounts for the Hessian matrix, which is the second derivative matrix of the objective function to be optimized (i.e., the performance criterion relative to image elements). The most popular techniques are variants of IR. Due to the large size of the Hessian matrix for image reconstruction, however, its structure (and that of its inverse) are typically ignored or poorly approximated. Furthermore, because of the wide distribution of eigen-values of the Hessian, current optimization techniques tend to show no improvement beyond a number of iterations (typically counted in the tens-to-hundreds) and may only cope with the large eigenvalues.

Multi-grid variations of these algorithms may help, but ultimately still fail because of the size of the Hessians involved with fine grids. Multi-grid resolution here refers to the use of progressively finer resolution as iterations are performed.

SUMMARY

The invention may provide a system comprising: one or more transmitters to transmit an excitation energy into an object under observation; one or more detectors to generate projection space data encoding an energy received by the one or more detectors in response to the transmitted excitation energy into the object under observation; a controller to control the one or more transmitters to transmit the excitation energy and the one or more detectors to generate the projection space data; and an image reconstructor to receive the projection space data and to process the projection space data by: computing a first quantity characterizing a difference between the projection space data and predicted projection data; computing a second quantity corresponding to at least one impulse response, each impulse response corresponding to a reference voxel of unit-intensity; computing an update value using the first quantity and an inverted function of the second quantity; and reconstructing an object space image representing the object under observation using the update value.

The invention may provide a workstation comprising: one or more processors; and one ore more data storage devices storing software to be executed by the one or more processors, the software comprising: software code to receive input data representing an object projected from an object space to a projection space; software code to compute a first quantity characterizing a difference between the input data and predicted projection data; software code to compute a second quantity corresponding to at least one impulse response, each impulse response corresponding to a reference voxel of unit-intensity at a location in the object space; and software code to compute an update value using the first quantity and an inverted function of the second quantity; and software code to reconstruct an object space image representing the object under observation using the update value.

The invention may provide a method implemented by one or more processors executing software code stored on one or more data storage devices, the method comprising: receiving input data representing an object projected from an object space to a projection space from at least one of a projection image acquisition system, the one or more data storage devices, another one or more data storage devices, a software simulation executed by the one or more processors, or a software simulation executed by another one or more processors; computing a first quantity characterizing a difference between the input data on a resolution grid and predicted projection data on the resolution grid; computing a second quantity corresponding to at least one impulse response, each impulse response corresponding to a reference voxel of unit-intensity at a location in the object space; computing an update value using the first quantity and an inverted function of the second quantity; reconstructing an image representing the object under observation using the update value, and outputting the reconstructed image to an output device, wherein the output device is at least one of the one or more data storage devices, another one or more data storage devices, a display device, or a printing device; wherein receiving the input data, computing the first quantity, computing the second quantity, reconstructing the image, and outputting the reconstructed image are performed by the one or more processors according to the software code stored on the one or more data storage devices.

BRIEF DESCRIPTION OF THE DRAWINGS

Exemplary embodiments will now be described in connection with the associated drawings.

FIG. 7A shows one X-ray projection during injection of iodine contrast dye into a beating hydraulic coronary phantom.

FIG. 7B shows the reconstructed image of the phantom obtained based on a method according to an exemplary embodiment of the invention.

DETAILED DESCRIPTION OF THE EMBODIMENTS

Exemplary embodiments of the invention are discussed in detail below. In describing exemplary embodiments, specific terminology is employed for the sake of clarity. However, the invention is not intended to be limited to the specific terminology so selected. A person skilled in the relevant art will recognize that other equivalent components may be employed and other methods developed without departing from the broad concepts of the invention. All references cited herein are incorporated by reference as if each had been individually incorporated.

Figure 1:
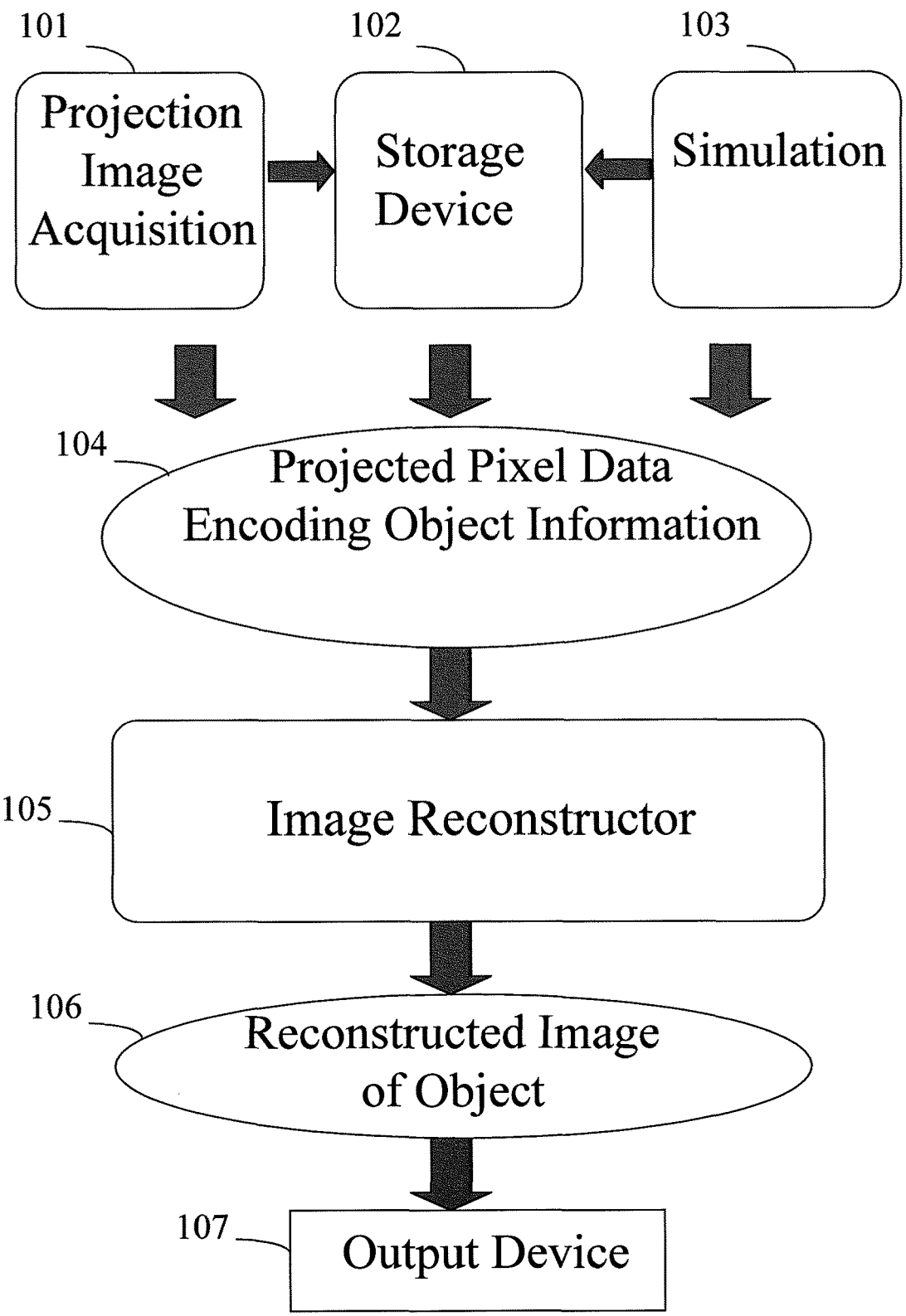
FIG. 1 shows a systematic chart according to an exemplary embodiment of the invention.

FIG. 1 shows a systematic chart according to some embodiments of the current invention. Projected pixel data 104 containing information encoding the internal structure of an object may be transformed using an image reconstructor 105 into a reconstructed image 106 to be visualized on an output device 107. The projected pixel data 104 may be from an experimental acquisition 101, or a simulation 103 on a computer, or a data storage device 102 containing recorded projected pixel data 104 from an earlier experiment or simulation. The experimental acquisition 101, data storage device 102, and simulation 103 may remotely provide the projected pixel data 104 to the image reconstructor 105 directly or via a network, for example, a local area network (LAN), a wide area network (WAN), the Internet, etc. Although only projected pixel data 104 is illustrated here, in general, the data may be the result of delivering any form of excitation energy into an object under observation and thus may include data from, for example, electron microscopy, magnetic resonance (MR), positron emission tomography (PET), single positron emission computed tomography (SPECT), ultrasound, fluorescence, multi-photon microscopy (MPM), optical coherence tomography (OCT), etc., in addition to computed tomography (CT). Data storage device 102 may be, for example, computer memory, CD-ROM, DVD, magneto-optical (MO) disk, hard disk, floppy disk, zip-disk, flash-drive, etc.

Figure 2:
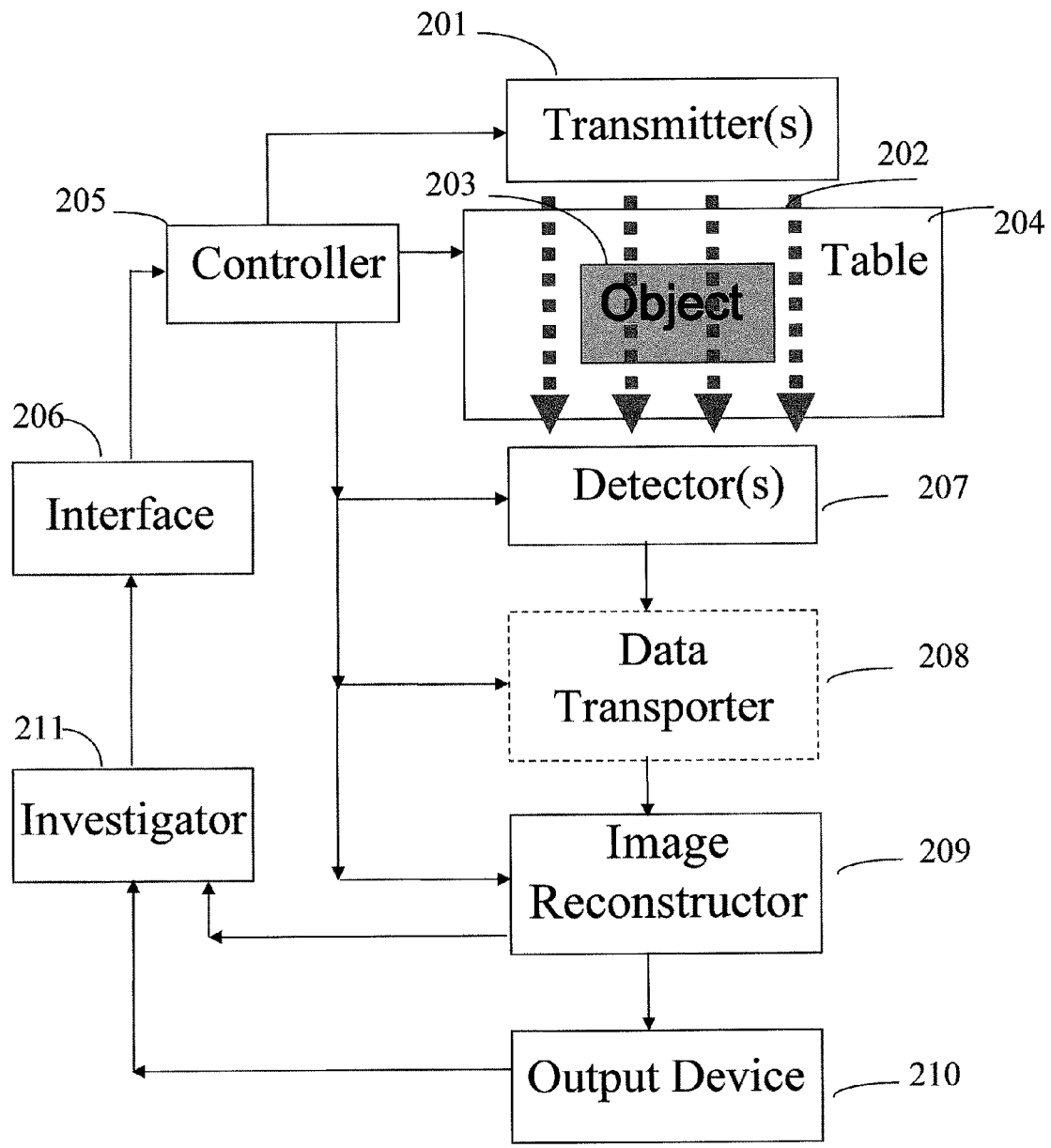
FIG. 2 shows an imaging system according to an exemplary embodiment of the invention.

FIG. 2 shows an imaging system according to some embodiments of the current invention. The imaging system may include: a controller 205; an interface 206 (e.g. a graphic user interface, keyboard, joystick, etc.) for signal communication with an investigator 211 (e.g., a human user, a computer, etc.) and synchronization with the controller 205; transmitter(s) 201 for generating and emitting excitation energy 202 in response to a control signal from the controller 205; and detector(s) 207 configured to generate projected pixel data 104. The projected pixel data 104 may be in a digital format stored in a storage device. The imaging system may also include: a translating or rotating table 204 configured for receiving an object 203 thereon and operable to translate or rotate in relation to the transmitter(s) 201 and the detector(s) 207; and an image reconstructor 105, 209 coupled electrically, or via an optional data transporter 208, such as the Internet, other networks, or a data bus, to the detector(s) 207 and the controller 205. A data bus, may be, for example, a subsystem of electrical wires that transfers data between computer components inside a computer or between computers. Although the data flow between connected components is uni-directional, the communication between connected components may be bi-directional.

Excitation energy 202 may be a form of radiation energy such as, for example, X-ray energy, electromagnetic (EM) energy, optical energy, infra-red (IR) energy, particle energy (e.g., electron, neutron, atom beams), vibration energy, such as ultrasound, etc. Excitation energy 202 may be irradiated onto an object 203, which may be, for example, a phantom, a human patient, a specimen, or any combination thereof. The excitation energy 202 may be emitted by transmitter(s) 201 of the corresponding energy type. The excitation energy 202 may propagate through the object 203 and a portion may be received by the appropriate detector(s) 207. The detector(s) 207 may convert received energy into measurable electrical signals that may be further convert the measured electrical signals into projected pixel data 104 in a digital format.

Controller 205 may be a circuit connected the transmitter(s) 201 and detector(s) 207 and may send control signals to the transmitter(s) 201 and detector(s) 207 to synchronize the transmission of the excitation energy 202 and the operation of the detector(s) 207. The circuit may be analog, digital, or mixed-signal. Controller 205 may also be a computer having one more processors and one or more memories to send control signals to the transmitter(s) 201 and detector(s) 207.

The image reconstructor 105, 209 may be responsive to the controller 205 and receptive of the projected pixel data 104 to reconstruct an image of the object 203 via a method according to some embodiments of the invention to produce a high fidelity image of the object with high computation efficiency. The image reconstructor 105, 209 may be a computer having one or more data storage devices storing software code to operate the computer according to the exemplary embodiments of the invention. The computer may include one or more processors and one or more memories to read and execute the software code stored on the one or more data storage devices. In another exemplary embodiment, the image reconstructor 105, 209 may include one or more program storage and execution devices operable according to the exemplary embodiments of the invention. The image reconstructor 105, 209 may produce the reconstructed image 106.

An output device 107, 210 may receive the reconstructed image 106. Output device 107, 210 may be a visualization device or a data storage device. A visualization device may be, for example, a display device or a printing device. Example display devices may include, for example, a cathode ray tube (CRT), a light-emitting diode (LED) display, a liquid crystal display (LCD), a digital light projection (DLP) monitor, a vacuum fluorescent display (VFDs), a surface-conduction electron-emitter display (SED), a field emission display (FEDs), a liquid crystal on silicon (LCOS) display, etc. Example printing devices may include, for example, toner-based printers, liquid ink-jet printers, solid ink printers, dye-sublimation printers, and inkless printers such as thermal printers and ultraviolet (UV) printers, etc. The printing device may print in three dimensions (3-D), such as a three-dimensional sculpting device.

The imaging system may further include investigator 211. Investigator 211 may be a human or a programmed computer to receive the reconstructed image 106 from an output device 210 or the image reconstructor 209 and then apply an algorithm (e.g., pre-programmed routine, artificial intelligence, machine learning, etc.) to extract diagnostic information about the object 203 or to fine-tune control parameters for transmitter(s) 201, detector(s) 207, table 204, image reconstructor 209, etc. In some embodiments, the interface 206 or the output device 210 may not be necessary. In some embodiments, the investigator 211, the controller 205, and the image reconstructor 105, 209 may reside on the same computer or separate computers.

Some embodiments of the invention may provide a workstation comprising one or more processors configured to reconstruct an image in a manner similar to image reconstructor 105, 209. The workstation may receive input data from at least one of an imaging system, a data storage device, or a computer. The input data may be received via a data bus, a cable, a wired network, a wireless network, etc. The workstation may further comprise an output device 107, 210 to receive the reconstructed image. The output device may be a data storage device, a display device, a printing device, etc. Example data storage devices, display devices, and printing devices are as discussed above.

Figure 3:
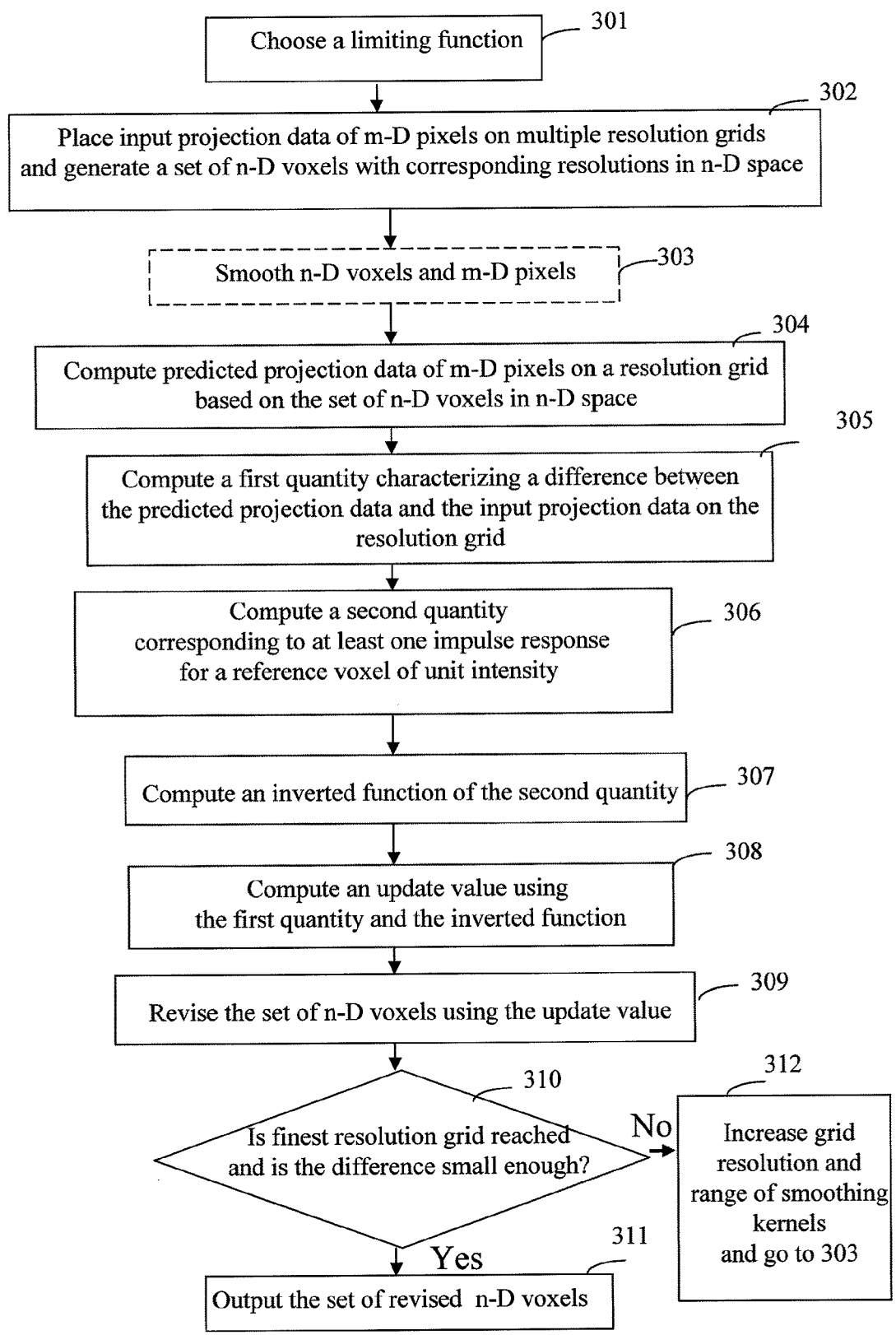
FIG. 3 shows a flow chart according to an exemplary embodiment of the invention.

FIG. 3 shows a flow chart of a method according to an exemplary embodiment of the invention.

In box 301, a suitable limiting (trimming) function f (x) may be chosen, such as, for example:

$$-a \leq f(x) \leq b \quad \text{Equ. (1)}$$

where $-a<0<b$ and for some neighborhood of x=0 the function f (x) is approximately x according to $$|f(x)-x| \leq \epsilon, \text{ for a suitable small } \epsilon > 0. \quad \text{Equ. (2)}$$

The function f may trim excessive values, especially at early iterations. For example, one such function is a tan(x). The limiting function may be relaxed and there may be no strict cut-off values a and b. Another example limiting function may be $h(x) = c \cdot x + (1-c) \cdot a \tan(x)$, $0 < c < 1$. Box, G. E. P., Jenkins, G. M., Time Series Analysis: Forecasting and Control, San Francisco, Calif.: Holden-Day, 1976, contains a selection of non-linear data transforms that may be used for function f.

In box 302, the input projection data 104 of m-dimensional (m-D) pixels may be placed on a series of resolution grids of varying resolutions (e.g., each subsequent resolution grid having fewer pixels than the previous one while maintaining the image range) for every given projection-direction. For example, a resolution grid in the series may have half the resolution of the previous one in the series. The coarsest size may be, for example, a single m-D pixel.

It is noted that usually 1<m<n and m may be equal for all projections. In general, however, m may vary with every projection and m>=0 (e.g., for certain noisy estimation problems).

Also in box 302, an initial set of n-dimensional (n-D) voxels may be placed in the n-D space so that their projections cover the available m-D projection pixels on the series of resolution grids. For example, a suitable set of values for these initial voxels may be a value corresponding to an average projection density; and for each voxel j, $v_{Lj} = \log(v_j)$ may be set. Monotonic functions other than the logarithm may be used. For example, an initial single n-D voxel density $v_i$ may be set equal to the average projection density.

In box 303, both the n-D voxels v and the m-D pixels p for the present grid resolution may optionally be smoothed with suitable kernels, where the m-D kernel is approximately the projection of the n-D kernel. This operation may correspond to the predictor algorithm (without the update) of the Kalman filter with noisy observations (where v is obtained from $v_L$). An example function may be, for example, $v = \exp(v_L)$. Other functions, including discontinuities, may be employed to account for additional density constraints. Exemplary smoothing kernels may have a Gaussian shape with a sigma-width, for example, between 0.4 and 2 voxel spacings. However, modifications are possible as will be discussed later with respect to box 307.

If desired, the voxels v may be constrained via a map to certain values. For example, in some regions, it may be known a-priori that the voxel density is zero. Also, in order to avoid numerical underflows for very small voxel densities, $v_{Lj}$ may be limited to a minimal negligible value. An exemplary limiting value may represent a density of about $10^{-15}$ of the maximal voxel density value $v_k^{max}$.

In box 304, predicted projection m-D pixels $p_p$ may be computed based on the set of n-D voxles v in n-D space. The predicted projection m-D pixels $p_p$ may be on a resolution grid from the series of resolution grids. If the grid resolution has been increased from a preceding resolution grid, predicted projections and voxel estimates v may be obtained via interpolation from the coarser/preceding resolution grid.

In box 305, a first quantity characterizing a difference between the predicted projection data and the input projection data 104 on the resolution grid may be computed.

If the projection pixel value $p_i$ of the input projection data 104 is greater than zero, the first quantity may be, for example, $$u_i = f(\log(L_i)) \quad \text{Equ. (3)}$$

where $L_i$ is an error ratio between measured $p_i$ of the input projection data 104 and predicted pixel value $p_{pi}$ of the predicted projection data, as expressed by, for example, $$L_i = p_i/p_{pi} \qquad \text{Equ. (4)}$$

Other suitable relations may be used for $L_i$ as well, such as, for example, functions where $L_i$ increases with $p_i$ and decreases with increasing $p_{pi}$. These functions may capture a measure of error between input projection data 104 and predicted projection data.

The log function above may be the logarithm of the error ratio, but may be a more general function of input vs. predicted projection values (e.g., functions used in the missing wedge problem in transmission electron microscopy).

If the projection pixel value $p_i$ of the input projection data 104 is no greater than zero, the first quantity may be, for example, $$u_i = -a. \qquad \text{Equ. (5)}$$

wherein a indicates a bound.

In box 306, a quantity corresponding to at least one impulse response $R_p$ for a reference voxel of unit intensity in n-D space may be computed. The impulse response $R_p$ may be computed for each desired reference n-D voxel for all p projections and back-projections, depending on the current resolution grid. The impulse response $R_p$ may depend on the location of the reference n-D voxel. The impulse response $R_p$ and its inverse may be computed either for each of the m-D projections or for the n-D voxels, depending on the preferred sequence of operations, which in turn may depend on the desired accuracy. This is analogous to FBP. A limited sub-set of reference n-D voxels may be selected for the evaluation of impulse response $R_p$. In some applications, as few as one n-D reference voxel at the center of the reconstruction space may be selected.

The impulse responses may be computed for the corresponding reference n-D voxels in several ways, and the inverses of these impulse responses may be used for subsequent combinations with the first quantity, as will be discussed later with respect to box 307.

In an exemplary embodiment, the impulse response $R_p$ at a particular location in a region of the n-D reconstruction/object space may be that of a linear system when a reference voxel of unit-intensity is considered.

When the center of this single reference n-D voxel at a particular location is projected into all p projection directions, p single-pixel projections (not necessarily all of the same dimensionality m) may be created. When these p projections are back-projected for reconstruction, a blurred version of the original voxel may be created. The blurred version may be linearly related to the original voxel, but may spread throughout the n-D space. This blurred function $R_p$ may be the impulse-response (or point spread function PSF) of the reconstruction system for this particular location.

For a finite reconstruction volume, this impulse response $R_p$ may depend on the location of the reference n-D voxel. For example, when the number of projections is small and the grid fine enough, the impulse response $R_p$ may be spider-like (e.g., it shows "spider-leg"-like extensions or streaks emanating from the "spider"-center location). Neighboring voxels may have similarly shaped "spider-leg"-like extensions but may be different length because the finite reconstruction region may cut the extensions at the boundaries. Furthermore, in geometries such as a cone-beam using p cone-beam projections, the directions and mutual angles of the "spider-legs" may change with location, as the "spider-legs" may point to the fixed tips of the p cones.

For purposes of approximations, however, slow spatial variations of these impulse response functions may be utilized to share the same impulse response function over a sufficiently small neighborhood of voxels in n-D space. Geometric considerations of the degree of similarity of "spider-legs" may determine the size of the well-matched voxel region that share the same approximate impulse response. An integral mismatch of, for example, several (e.g., tens of) percent at the endpoints of the "spider-legs," relative to their content, may be quite acceptable, especially when subsequent iterations may correct these errors. In contrast, FBP methods usually do not consider this truncation effect, while matrix formulations, such as shown in Wood do.

Also in box 306, the impulse response $R_p$ for a given voxel may then be combined with contributions from a noise variance to obtain R, which would then be the second quantity. The input projection data may be measured to obtain the noise variance. This combination may increase the value at the "spider" center. R and its inverse may be computed either for each of the m-D projections or for the n-D voxels, depending on the preferred sequence of operations, which in turn may depend on the desired accuracy. Smaller increases, such as when the assumed noise level is low, may significantly increase the requirements for precise computation of the inverse of R (corresponding to, for example, the Kalman/Wiener filter gain). Conveniently, however, the computation on multiple resolution grids may keep the signal-portion in the residual projection errors at modest/low levels, thus supporting efficient computation of $R^{-1}$. The signal portion may be the structural information in the residual projection errors not accounted for by the noise variance measured from the input projection data.

In box 307, the computed second quantity may then be inverted to obtain P, expressed as, for example, $P=R^{-1}$ (in lieu of using the inverse Hessian). This step may be performed in the Fourier domain. Exemplary embodiments of the invention may characterize the inverted function as a Kalman or Wiener gain in the Fourier domain, as discussed below.

An observation model for measured input projection data Y may be, for example, $Y = H X + W$, wherein X may represent the object density, H may represent the system transform function, and Y may represent the input projection data 104.

In matrix notation, X may be estimated from available data Y. The data Y may include contributions from measurement noise. X may have the following statistical properties:

$$X_0 = E[X], \text{ and} \qquad \text{Equ. (6)}$$

$$V_X = E[(X-X_0) \cdot (X-X_0)^t] \qquad \text{Equ. (7)}$$

where $X_0$ is the expectation E (i.e., average) of X and $V_X$ is the covariance matrix of the object density X.

The projection noise W may be expressed as:

$$E[W] = 0, \qquad \text{Equ. (8)}$$

$$V = E[W \cdot W^t], \text{ and} \qquad \text{Equ. (9)}$$

$$E[W \cdot X^t] = 0 \qquad \text{Equ. (10)}$$

where V is the covariance matrix of the projection noise W.

The minimum variance (Kalman) gain, K, as discussed, for example, in Sage (Sage, A. P., J. L. Melsa, Estimation Theory with Applications to Communications and Control, New York: McGraw-Hill, 1971, page 262), may be given by $$K = V_X H^t [H V_X H^t + V]^{-1} = V_X H^t R_Y^{-1} \qquad \text{Equ. (11)}$$

or by $$K = \{H^t [I + V(H V_X H^t)^{-1}]\}^{-1} \qquad \text{Equ. (12),}$$

provided $HV_XH^t$ is invertible. This condition may be satisfied in the early low-resolution iterations of the suggested computations where the number of pixels in the input projection data may exceed the number of estimated image voxels. In the context of tomography, $R_Y^{-1}$ may be too large for inversion, but Equation (12) may suggest useful modifications of H to obtain practical K. Per Equation (11), providing a full-rank V may remove possible zero eigenvalues from the matrix $R_Y^{-1}$. The relation between $H V_X H^t$ and V may determine to what degree the estimation of the image X may rely on the prior statistics of X.

Using complex spectral notation, the power-spectral density of an object may be $S_{XX}$, the observation transfer filter may be H, the projection noise spectral power density may be $S_{VV}$, and the Wiener (see, for example, Wiener, Norbert, *Extrapolation, Interpolation, and Smoothing of Stationary Time Series*. New York: Wiley, 1949) gain may be expressed as:

$$W = H * S_{XX}/(H * S_{XX} H + S_{VV}) \quad \text{Equ. (13)}$$

$$= [H(U + S_{VV}/(H * S_{XX} H))]^{-1} \quad \text{Equ. (14)}$$

where * is the conjugate function and U is the unit transfer function.

Spectral formulations may be computationally feasible for tomographic applications. In tomographic reconstructions, the uncertainty of the object density (e.g., $S_{XX}$ or $V_X$ may be relatively large) may dominate the projection noise (e.g., $S_{VV}$ or V may be relatively small) and the major task of finding a Wiener gain W (or Kalman gain K) may be to find useful approximations to Equation (13) (or equivalently Equation (11)).

Thus, the input projection data 104 may be measured to obtain the V as well as $V_X$, as expressed above. $H V_X H^t$ and $H * S_{XX} H$ may be computed, for example, based on measured $V_X$. The contributions from a noise variance mentioned in box 306 may refer to contributions due to, for example, V, $H V_X H^t$, or $H * S_{XX} H$. Although Equation (12) for the Kalman gain and Equation (14) for the Wiener filter gain may be computed directly, further simplification may be possible. For example, for small cross-correlation of the measurement noise W (e.g., V may be diagonally dominant) and modest cross-correlation of the projected object densities (e.g., $H V_X H^t$ may be diagonally dominant, especially during the iterative process), the compound expression of Equation (12) or (14) may be simplified by computing the gains block-wise for the individual (or groups of) projections. For example, block-wise processing may be further simplified by using inverses of, for example, modified local impulse responses on a voxel-by-voxel (n-D processing) or pixel-by-pixel (m-D approximate processing) basis. The modification of the local impulse responses may be given by, for example, the elements of the noise-to-signal structure $V (HV_X H^t)^{-1}$ seen in Equation (12), or similarly by $S_{VV}/(H * S_{XX} H)$ seen in Equation (14). The modification may be applied on a voxel-by-voxel basis. The modification may be approximated by increasing the value of the "spider" central region (e.g., near the peak of the impulse response function, corresponding to the (near-) diagonal elements of the matrix $V (H V_X H^t)^{-1}$ in Equation (12) or $S_{VV}/(H * S_{XX} H)$ in Equation (14)). In the case of W being white noise and projected object uncertainty being white with an estimated root mean square (RMS) noise-to-signal ratio of r, the spider center may be increased, for example, by a factor of $(1+r^2)$. After this modification, Kalman gain and Wiener filter gain may be computed by numerical inversion according to, for example, Equations (12) and (14).

It is noted that $R_P$, as discussed above, is related to the above-noted matrix (or transfer filter) H as expressed in Equations (11) and (13). The processing sequence may be changed by breaking the single step expressed in the Kalman gain K or Wiener gain W into two steps of vector-operations. The two steps may be first back-projecting, for example, projection data and then filtering with an n-D filter $P_K = R_K^{-1}$ of reference voxel K; some neighborhood surrounding voxel K may use the resulting filter output. The two steps may also be first pre-filtering, for example, the projection data with p m-D filters $P_{iK}$ ($0 <= i < p$), where each $P_{iK}$ may be obtained from the inversions of the projections of the n-D impulse response (PSF) $R_{PK}$ modified by noise-to-signal ratio and then back-projecting the filter outputs; again, some neighborhood surrounding voxel K (or its projections) may use the resulting filter output (update). To cover the entire n-D space several voxel locations and their neighborhoods may be used. Thus, the inversion of an exceedingly large matrix shown in Equations (11) and (13) may be decomposed into the inversions of a modest set of much smaller number sets $R_K$, where each $R_K$ may vary only slowly in the object space, allowing repeated use. Furthermore, each $R_K^{-1}$ for a reference voxel may be computed very efficiently by Fourier techniques.

Overall, two aspects of the approximations used to compute gain P may contribute to high statistical efficiency.

First, for low frequencies, the Kalman/Wiener filter gain (now replaced by the gain P) may be estimated by adding a small constant at the origin of the impulse response function that may account for the noise-to-signal ratio over a sufficiently wide frequency range. A small neighborhood near the center of the impulse response function may be modified to account for, for example, "pink" measurement noise by adding a "narrow" Gaussian bell rather than just a constant at the origin.

Second, for higher frequencies, the filter corresponding to gain P may be tapered/smoothed as characterized by the high frequency signal-to-noise ratio. In order to improve numerical accuracy, this tapering/smoothing function may be performed on the update of the image density and/or the estimated image density on the current resolution grid. Low-pass filtering of the estimated image density, at every stage during the iterative computations on the series of resolution grids, may help tapering off high-frequency image components, reducing the computational burden.

In box 308, an update value may be computed using the first quantity and P. For example, P may be combined with the first quantity to obtain a raw update value i for the given voxel (or pixel) image element. For example, P may be convolved with the first quantity to obtain the raw update value. With P varying slowly in the n-D reconstruction space, computing time may be saved by applying P as an approximation to a suitable, yet sufficiently small, neighborhood of the given voxel. A limiting function g, constructed similar to fin Equations (1) and (2) discussed above, may then be applied to the raw update value i to obtain modified update value $i_g = g(i)$. This modification may protect against excessive corrections. During development of exemplary embodiments of the invention, many experiments directly using the raw update value failed. The inventor then conceived and developed limiting functions and judicious use thereof to limit excessive update values. The modified update may be the update value for subsequent processing.

In boxes 304-308, an additional consideration for simplification may be helpful for cone-beam geometry reconstruction (e.g., as used in angiography), in which the number of projections p may be small (p<<N, where N may represent the number of voxels along a representative projection path through the reconstruction volume). In this case, the individual "spider-legs" may be distinct, especially during the high-resolution final stages of the multiple reconstruction grids. Computing the impulse response $R_P$ for many small regions in this high-resolution n-D space may be time consuming. As an approximation of using the n-D impulse response, p lower-dimensional projected impulse responses of dimension $m_i$ ($0<=i<p$) may be used. Their corresponding modified inverses or Kalman/Wiener gains may then be applied iteratively to the individual error-images of the projections. These m-D impulse responses may be the projections of the above-noted n-D impulse response, which may be spider-like, onto the respective m-D projection space. Their properties may be as described above, namely, slowly varying in the projection space. The computational burden, however, for computing the impulse responses of p projections, the inverses of these computed impulse responses, and the subsequent convolutions (now applied to the m-D projections) may be much less than computing them in the n-D space, especially when p<<N. The computed impulse responses may be modified in a manner similar to that of R. The computed impulse responses may also be band-pass filtered to reduce noise in the tomographic reconstruction. This technique for tomographic inversion may be similar to filtered back-projection where the projections themselves are filtered prior to reconstruction. This technique may not be limited to cone-beam geometry but may be applied to other geometries as well, such as, for example, parallel beam geometry.

In box 309, the modified update value $i_g$ may be added to the value of the corresponding image density in the set of n-D voxels v to revise the set of n-D voxels v. The addition may be bounded by a limiting function similar to Equations (1) and (2) discussed above. The addition may be performed for a portion of the entire set of n-D voxels. For accuracy, the voxel values v may be scaled so that their projections best match the raw image data.

In box 310, if the resolution grid is the finest and if the differences (e.g., the residuals) between the computed predictions and the input projection data are (statistically) small enough, the revised set of n-D voxels representing density estimate v, $v_L$, or both, (and, if desired, the estimated predictions and errors) may then be output to an output device, as shown in box 311. Smoothing may be applied prior to outputting. Otherwise, the resolution grid may be changed to a resolution grid having a larger size than the current resolution grid (or possibly the severity/range of the n-D smoothing kernel may be decreased) and in box 312, the flow may go to box 303.

Upon termination in box 311, a high fidelity reconstructed image of the object 106 may be obtained. This reconstructed image 106 may reveal internal information of the object 203 non-invasively and non-destructively, having a wide range of applications in diagnostic medical imaging and non-destructive evaluation. The reconstructed image 106 may be visualized on a visualization device or stored in a computer memory or storage medium, as discussed above for output device 107.

Figure 4B:
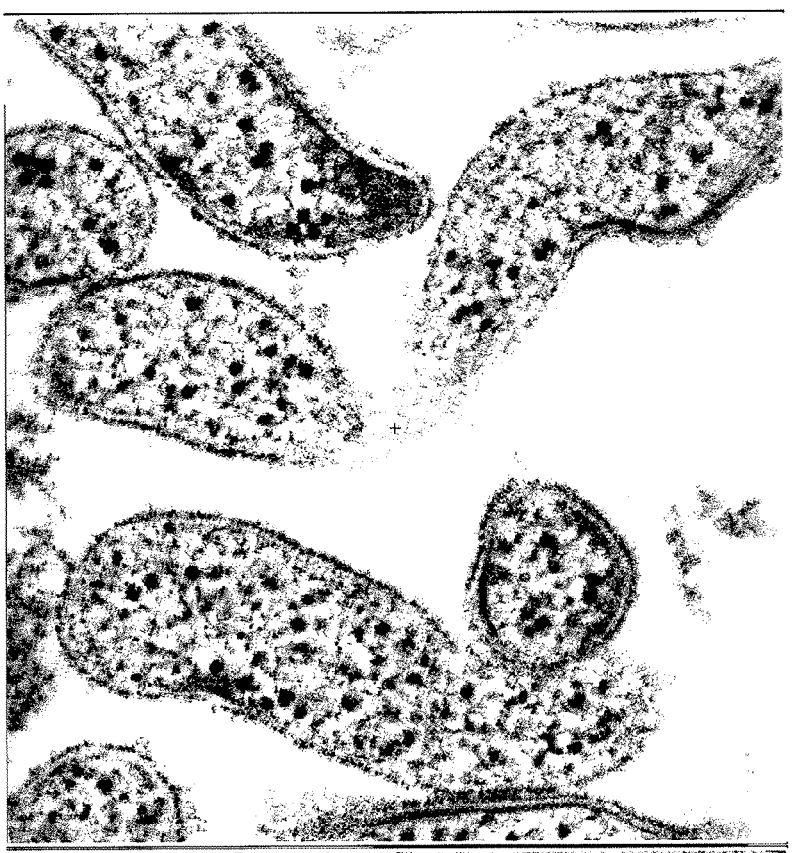
FIGS. 4A and 4B, respectively, show reconstructed images of cells based on a conventional filtered back-projection (FBP) reconstruction and a method according to an exemplary embodiment of the invention.
Figure 4A:

Projected pixel data 104 from Trachtenberg, S., Dorward, L. M., Speransky, V. V., Jaffe, H., Andrews, S. B., Leapman, R. D., "*Structure of the Cytoskeleton of Spiroplasma melliferum BC3 and Its Interactions with the Cell Membrane*," J. Mol. Biol., 378, pp. 776-787, 2008, was used to demonstrate the improvement attainable via an exemplary embodiment of the invention. FIG. 4A shows a reconstructed image 106 based on filtered back-projection (FBP) reconstruction of the projected pixel data 104. FIG. 4B shows the reconstructed image 106 according to an exemplary embodiment of the invention. A comparison between FIGS. 4A and 4B demonstrates a superior image clarity in FIG. 4B as measured by sharper contrast of various densities such as intracellular vs. extracellular space, cell membranes, ribosomes, detail of the spiroplasma, etc. The image in FIG. 4B is more desirable to a user. Both reconstructions used approximately 166 double-tilt transmission electron microscopy (TEM) projections over a range of approximately ±70 degrees.

Figure 5:
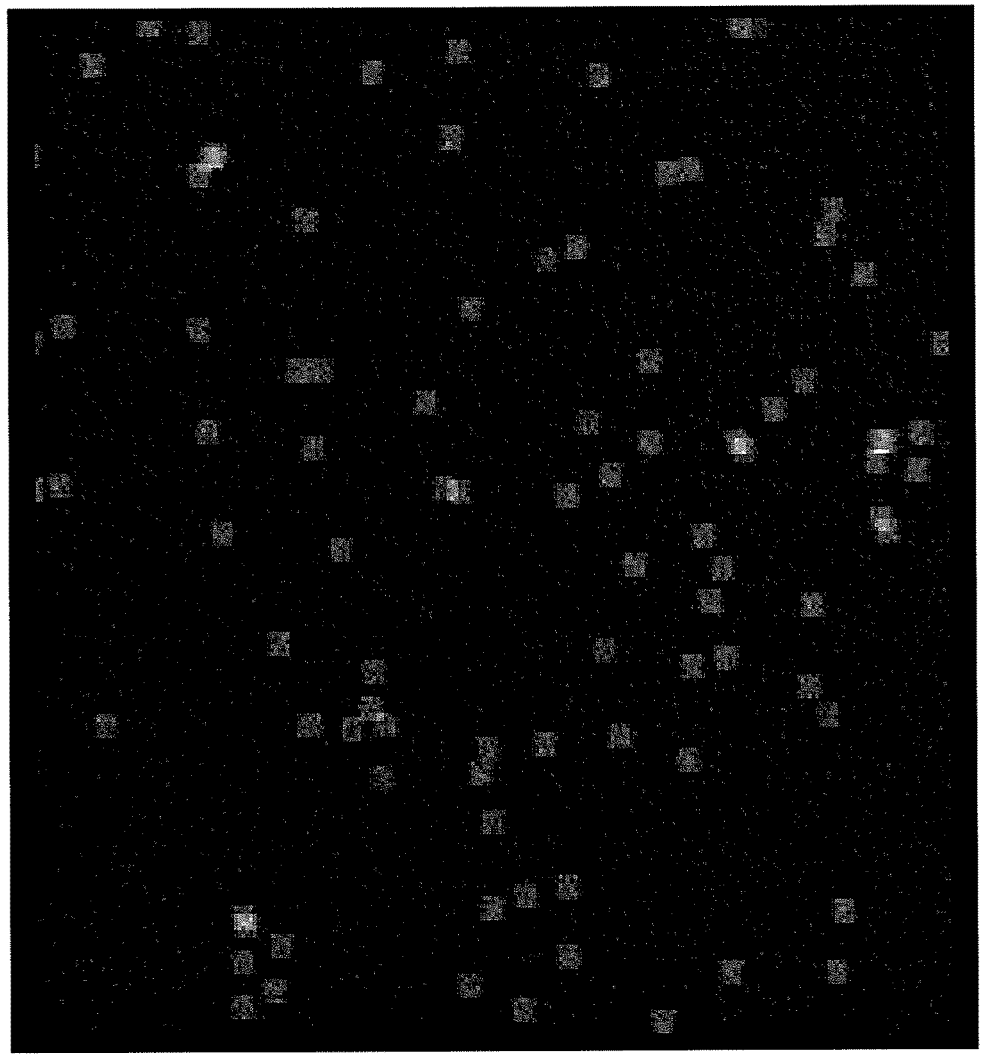
FIG. 5 shows an en-face sample projection of a simulated phantom.

FIG. 5 shows an en-face sample projection of a simulated phantom. The simulated phantom contains some 100 cubes of size 6×6×6 voxels at random locations in a 3-D box of size 256×256×64 voxels. The voxels have a density of 5 units embedded in a surrounding density of 0.85 units. A total of 49 projections (single tilt, +/−72 degrees) with added white noise were obtained by a computer simulation 103 to generate the projected pixel data 104.

Figures 6A, 6B:
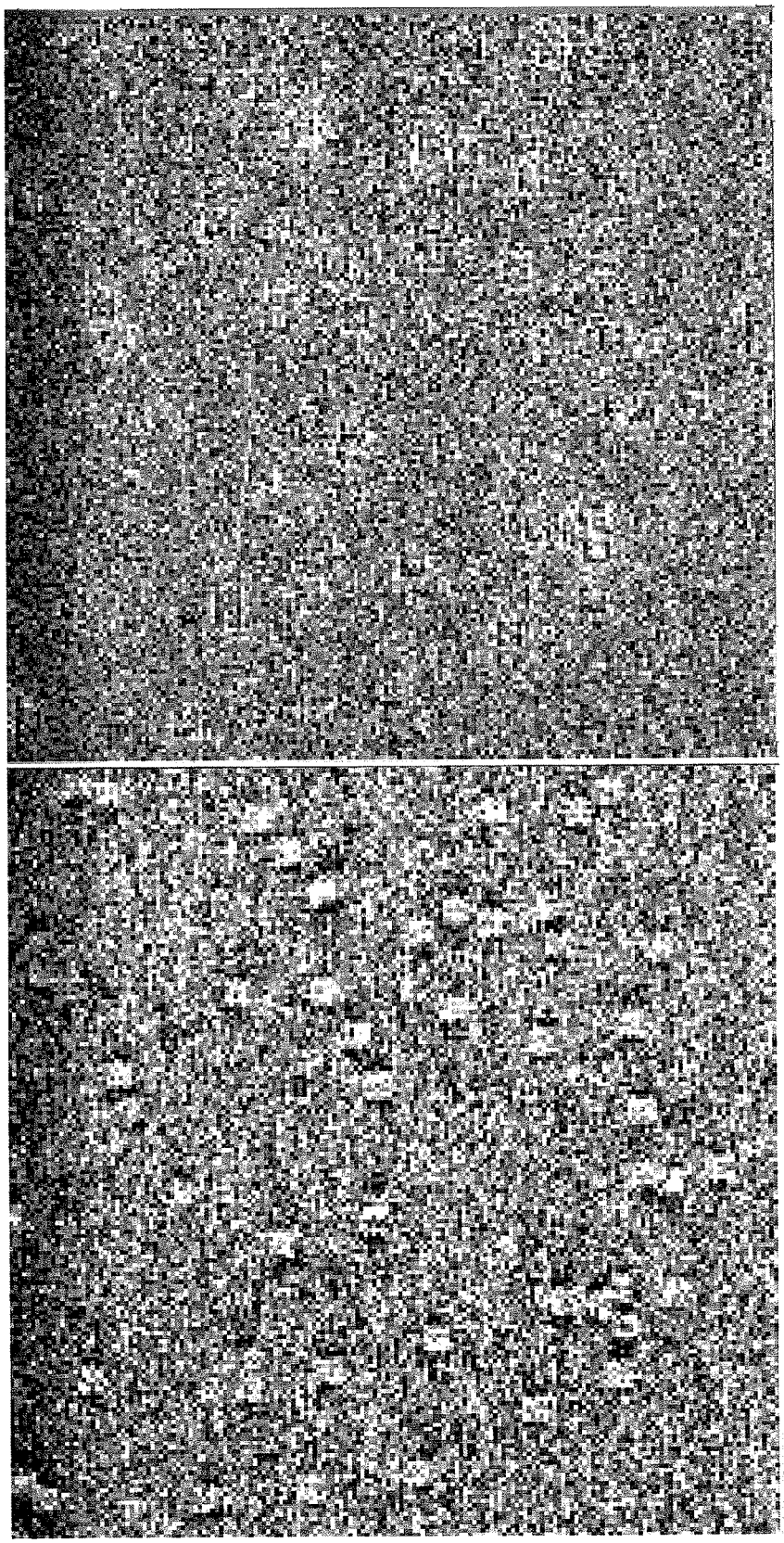
FIGS. 6A and 6B, respectively, show the reconstruction error based on the simultaneous iterative reconstruction technique (SIRT) and a method according to an exemplary embodiment of the invention.

According to the well-known gold standard in statistical model validation, reconstruction quality may be most critically evaluated by examination of residues, i.e., the discrepancy between the truth (for example, the simulated phantom in FIG. 5, known a priori) and the reconstructed image 106. A high-fidelity reconstruction may lead to residues that are random and contain very little contributions from the structure of the 3-D objects (e.g. cubes in the simulated phantom in FIG. 5). FIG. 6A shows the residues of simultaneous iterative reconstruction technique (SIRT), while FIG. 6B shows those obtained from a method according to an exemplary embodiment of the invention. The rather striking residual square patterns in FIG. 6A (after 15 iterations) and the dominant white noise appearance in FIG. 6B (after one high resolution iteration) further demonstrate the superiority of the invention in image fidelity and computation efficiency. The iterations count for SIRT was optimized for this example because more or fewer iterations for SIRT only led to degradation in the image quality.

The invention may also apply to situations where the number of projections is small, for example, cone-beam geometry in angiography. FIG. 7A shows one X-ray projection during injection of iodine contrast dye (as customarily employed in, for example, interventional cardiac subtraction angiography) into a beating hydraulic coronary phantom made of plastic tubes. The projected pixel data 104 used was from only 6 digital subtraction projections of the underlying phantom due to the transient nature of injection. FIG. 7B shows the reconstructed image 106 via an exemplary embodiment of the invention, which accurately represents the geometry of the beating hydraulic phantom. The reconstructed image may not be obtained by filtered back projection (FBP) or simultaneous iterative reconstruction technique (SIRT) or even maximum entropy (MENT) method as the number of projections is unusually small and/or the number of iterations becomes impractical with current computing resources.

As discussed above, some exemplary embodiments of the invention combine computational/processing techniques and result in a rapid and accurate computation/estimation of the desired n-D voxels in the region of interest while allowing arbitrary m-D projections (and directions) to be utilized. It is noted that m may not be fixed, and it may depend on the projection index. The efficiency of the combination of techniques may apply to a wide range of projection numbers. The efficient use of the available projection (measurement) information may make the method effective both when the number of projections is very large and when it is limited (small or incomplete), such as in coronary angiography.

The inventive non-linear inversion technique may combine: (i) a linearization of certain parts of a non-linear Kalman filter (approximating Bayesian estimation) through decomposition of the n-D image estimate into two non-linearly related domains within the region of reconstruction; (ii) a multi-grid computation comparable to "stair-cases" with further subdivision of resolution by using decreasing degrees of image smoothing (comparable to "steps"); and (iii) when needed, efficient computation of the inverse impulse responses (or transfer function) of linear systems modified by estimates of image noise in lieu of using the inverse Hessians, yielding the approximate Kalman/Wiener filter gain for selected regions in the object space.

In particular, the non-linear Kalman filter has been discussed in Jarisch W. R. & Detwiler J. S., "Statistical Modeling of Fetal Heart Rate Variability," IEEE Trans. On Biomed. Eng., Vol. BME-27, No. 10, pp. 582-589, October 1980, and the application of Kalman filtering for image reconstruction in Jarisch W., *Determination of Material Properties by Limited Scan X-ray Tomography*, Technical Report USAF AFWAL-TR-81-4050, Wright-Patterson Air Force Base, Ohio 45433, 1981. Alternative methods, such as, for example, FBP, FFT, and Wiener filter, may be used in place of the linear portions of the inversion. Either of the two non-linearly related domains within the region of reconstruction may represent the Kalman system state.

By the above combination, an efficient error reduction, similar to the effective use of the Hessian in optimization, may be achieved with every iteration. The achieved efficiency may be close to that of quadratic convergence. This approach may bypass the severe issues of high dimensionality and poor convergence rate encountered in approaches taken by others, such as, for example, those in Kolehmainen, V., Brandt, S. S., *Structure-From-Motion Without Correspondence From Tomographic Projections by Bayesian Inversion Theory*, IEEE Trans. Medical Imaging, ITMID4, Vol. 26, No. 2, pp. 238-248, February 2007.

Alternatively, an exemplary embodiment of the invention may be viewed as a combination of IR with (space variable/non-stationary/segmented) FBP, termed S-FBP herein. There may be one or several segments associated with the S-FBP, depending on the requirements of approximations. In general, the FBP would not be stationary over the field of reconstruction. Slow changes of the field properties, however, may allow approximations by breaking the field of reconstruction into overlapping regions/segments with weighted transitioning between those regions. The speed, efficiency, and flexibility of S-FBP may be achieved through a suitable selection and combination of several implementations as discussed below.

For example, the S-FBP part may be applied to non-linearly transformed data, rather than the raw projection data.

For example, multi-grid computation may support linearization and keep the operations count at each iteration very low. For example, the total operations count prior to the final computation on the finest resolution grid may be lower than that of S-FBP on the finest resolution grid.

For example, the voxel-density may be represented in two non-linearly related domains (connected via a map): one for updating via S-FBP (which may be variable in the n-dimensional space, depending on the desired approximation techniques), and one for computing projection-predictions. The filter weights of the S-FBP part may depend on voxel location, but grouping voxels together for use with the same weights may improve the computational efficiency.

For example, arbitrary projection dimensionality and directions may be used by computing the filter-weights of the S-FBP part from the inverse of the linearized system impulse response (or transfer function). The linearized system impulse response (or transfer function) may have been combined with a noise variance determined from measurements of the input projection data.

For example, suitably chosen limiting (trimming) functions may protect against numerical singularity and instability during computation.

For example, suitably chosen smoothing functions, applied judiciously to voxel and pixel values at each iteration, may contribute to the stability and accuracy of numerical computation. This smoothing of voxel and pixel values may be functionally comparable to the Kalman predictor algorithm prior to generating the update values. The iterative application of smoothing may be similar to the state predictor algorithm in a Kalman filter.

Because the accuracy of the iterations preceding the computation on the finest resolution-grid may be sufficient, iterating through the finest resolution-grid may not be necessary computationally, and therefore computation of the error-correction terms may be saved. In these instances, the speed of reconstruction may become comparable to that of the S-FBP. This may be because the computation on the finest resolution-grid may achieve an operations count comparable (within a factor>1) to that of FBP, while the combined operations-count for all the preceding lower-resolution iterations on coarser resolution grids may be less than that of the computation on the finest resolution grid, especially for higher dimensional image reconstructions.

Exemplary embodiments of the invention, as discussed with respect to the method shown in FIG. 3, may be provided as software code stored on a data storage device, such as, for example, CD-ROM, DVD, magneto-optical (MO) disk, hard disk, floppy disk, zip-disk, flash-drive, etc. The stored software code may be readable and executable by a computer having one or more processors, one or more memory devices, such as, for example, random-access memory (RAM) devices, dynamic RAM (DRAM) devices, flash memory devices, and static RAM (SRAM) devices, etc., to perform the exemplary method as discussed above with respect to FIG. 3.

Exemplary embodiments of the invention may provide one or more program storage and execution devices, for example, application specific integrated circuits (ASICs). field programmable gate arrays (FPGAs), complex programmable logic devices (CPLDs), application specific instruction-set processors (ASIPs), etc. for storing and executing the exemplary method as discussed above with respect to FIG. 3.

The examples and embodiments described herein are non-limiting examples.

The invention is described in detail with respect to exemplary embodiments, and it will now be apparent from the foregoing to those skilled in the art that changes and modifications may be made without departing from the invention in its broader aspects, and the invention, therefore, as defined in the claims is intended to cover all such changes and modifications as fall within the true spirit of the invention.

What is claimed is:

1. A system comprising:
   one or more transmitters to transmit an excitation energy into an object under observation;
   one or more detectors to generate projection space data encoding an energy received by the one or more detectors in response to the transmitted excitation energy into the object under observation;
   a controller to control the one or more transmitters to transmit the excitation energy and the one or more detectors to generate the projection space data; and an image reconstructor to receive the projection space data and to process the projection space data by:
  computing a first quantity for each of a plurality of object space voxels, the first quantity characterizing a logarithm of a ratio between a value of the projection space data and a corresponding value of predicted projection data;
  computing a second quantity for each of the plurality of object space voxels, the second quantity corresponding to at least one inverted impulse response combined with contributions from a noise variance, each impulse response corresponding to a reference voxel of unit-intensity, the second quantity computed using the contributions from the noise variance and at least one of a Kalman filter gain, an approximate Kalman filter gain, a Wiener filter gain, or an approximate Wiener filter gain;
  computing an update value for each of the plurality of object space voxels, each update value computed using the corresponding first quantity and the corresponding second quantity; and
  reconstructing an object space image representing the object under observation using the update values.

2. The system according to claim 1, wherein the excitation energy is at least one of electromagnetic (EM) energy, X-Ray energy, particle beams, infra-red energy, optical energy, or vibration energy.

3. The system according to claim 1, wherein the predicted projection data is computed based on a set of the object space voxels, wherein the set of the object space voxels covers a plurality of resolution grids of varying sizes when the set of the object space voxels are projected to projection space.

4. The system according to claim 3, wherein computing an update value using the first quantity and the second quantity comprises:
  convolving a weighting of the first quantity with the second quantity.

5. The system according to claim 1, wherein reconstructing the object space image representing the object under observation using the update value comprises:
  revising data in a set of the object space voxels with the corresponding update values.

6. The system according to claim 1, further comprising:
  an output device to receive the object space image representing the object under observation, wherein the output device is at least one of a data storage device, a display device, or a printing device.

7. The system according to claim 1, further comprising:
  an investigator computer to receive the object space image and programmed to perform extraction of diagnostic information from the object space image or to fine tune parameters for at least one of the one or more transmitters, the one or more detectors, or the image reconstructor.

8. The system according to claim 1, wherein the image reconstructor to receive the projection space data and to process the projection space data further comprises processing the projection space data by:
  smoothing at least one of the prediction space data and a set of object space voxel data.

9. The system according to claim 1, wherein computing the second quantity comprises at least one of:
  back-projecting the projection space data for a neighborhood around the reference voxel to produce one or more back-projected outputs, and inverting the one or more back-projected outputs combined with the contributions from the noise variance; or
  inverting projections of the impulse response modified by a signal-to-noise ratio.

10. One or more program storage and execution devices comprising:
  one or more processors; and
  one or more data storage devices storing software to be executed by the one or more processors, the software comprising:
    software code to receive input data representing an object projected from an object space to a projection space;
    software code to compute a first quantity for each of a plurality of object space voxels, the first quantity characterizing a logarithm of a ratio between a value of the input data and a corresponding value of predicted projection data;
    software code to compute a second quantity for each of the plurality of object space voxels, the second quantity corresponding to at least one inverted impulse response combined with contributions from a noise variance, each impulse response corresponding to a reference voxel of unit-intensity at a location in the object space, the second quantity computed using the contributions from the noise variance and at least one of a Kalman filter gain, an approximate Kalman filter gain, a Wiener filter gain, or an approximate Wiener filter gain;
    software code to compute an update value for each of the plurality of object space voxels, each update value computed using the corresponding first quantity and the corresponding second quantity; and
    software code to reconstruct an object space image representing the object under observation using the update values.

11. The one or more program storage and execution devices according to claim 10, wherein the input data is received from at least one of a projection image acquisition system, the one or more data storage devices, another one or more data storage devices, a software simulation executed by the one or more processors, or a software simulation executed by another one or more processors.

12. The one or more program storage and execution devices according to claim 10, wherein the input data is received via a data bus, a cable, a wired network, or a wireless network.

13. The one or more program storage and execution devices according to claim 10, further comprising:
  an output device to receive the image, wherein the output device is at least one of the one or more data storage devices, another one or more data storage devices, a display device, or a printing device.

14. The one or more program storage and execution devices according to claim 10, wherein the software further comprises software code to convolve a weighting of the first quantity with the second quantity.

15. The one or more program storage and execution devices according to claim 10, wherein the software further comprises software code to smooth at least one of the prediction space data and a set of object space voxel data.

16. The one or more program storage and execution devices according to claim 10, wherein computing the second quantity comprises at least one of:
  back-projecting the projection space data for a neighborhood around the reference voxel to produce one or more back-projected outputs, and inverting the one or more back-projected outputs combined with the contributions from the noise variance; or inverting projections of the impulse response modified by a signal-to-noise ratio.

17. A method implemented by one or more processors executing software code stored on one or more data storage devices, the method comprising:
receiving input data representing an object projected from an object space to a projection space from at least one of a projection image acquisition system, the one or more data storage devices, another one or more data storage devices, a software simulation executed by the one or more processors, or a software simulation executed by another one or more processors;
computing a first quantity for each of a plurality of object space voxels, the first quantity characterizing a logarithm of a ratio between a value of the input data on a resolution grid and a corresponding value of predicted projection data on the resolution grid;
computing a second quantity for each of the plurality of object space voxels, the second quantity corresponding to at least one inverted impulse response combined with contributions from a noise variance, each impulse response corresponding to a reference voxel of unit-intensity at a location in the object space, the second quantity computed using the contributions from the noise variance and at least one of a Kalman filter gain, an approximate Kalman filter gain, a Wiener filter gain, or an approximate Wiener filter gain;
computing an update value for each of the plurality of object space voxels, each update value computed using the corresponding first quantity and the corresponding second quantity, wherein the second quantity is combined with the first quantity and contributes to a logarithmically transformed non-negative preliminary object density;
reconstructing an image representing the object under observation using the update values, and
outputting the reconstructed image to an output device, wherein the output device is at least one of the one or more data storage devices, another one or more data storage devices, a display device, or a printing device;
wherein receiving the input data, computing the first quantity, computing the second quantity, computing the update value, reconstructing the image, and outputting the reconstructed image are performed by the one or more processors according to the software code stored on the one or more data storage devices.

18. The method according to claim 17, wherein the resolution grid is obtained from a plurality of resolution grids of varying sizes.

19. The method according to claim 18, wherein the predicted projection data is computed based on a set of the object space voxels, the set of the object space voxels covers the plurality of resolution grids of varying sizes when the set of the object space voxels are projected to projection space.

20. The method according to claim 19, further comprising:
smoothing with a smoothing kernel at least one of the input data on the resolution grid or the set of the object space voxels.

21. The method according to claim 19, wherein one or more characteristics of the set of the object space voxels are constrained within one or more ranges of values.

22. The method according to claim 17, wherein the first quantity is characterized as a measure of error between the input data and the predicted projection data.

23. The method according to claim 17, wherein the second quantity includes contributions from a noise variance obtained from measurements of the input data.

24. The method according to claim 17, wherein the second quantity is computed for a surrounding volume covering the location of the reference voxel of unit-intensity in the object space or for projections of the reference voxel of unit-intensity in the object space, including a surrounding volume of the reference voxel.

25. The method according to claim 17, wherein reconstructing the image comprises:
convolving a weighting of the first quantity with the second quantity to obtain the update value.

26. The method according to claim 17, wherein the update value is further limited by a limiting function.

27. The method according to claim 17, further comprising:
revising densities in a set of the object space voxels using corresponding update values.

28. The method according to claim 27, further comprising:
changing to a different resolution grid having a larger size than the resolution grid after the set of the object space voxels is revised.

29. The method according to claim 17, further comprising:
smoothing at least one of the prediction space data and a set of object space voxel data.

30. The method according to claim 17, wherein computing the second quantity comprises at least one of:
back-projecting the projection space data for a neighborhood around the reference voxel to produce one or more back-projected outputs, and inverting the one or more back-projected outputs combined with the contributions from the noise variance; or
inverting projections of the impulse response modified by a signal-to-noise ratio.

31. A storage device storing software for execution by one or more processors, the software, when executed, causes the one or more processors to:
receive input data representing an object projected from an object space to a projection space from at least one of a projection image acquisition system, the storage device, another one or more data storage devices, a software simulation executed by the one or more processors, or a software simulation executed by another one or more processors;
computing a first quantity for each of a plurality of object space voxels, the first quantity characterizing a logarithm of a ratio between a value of the input data on a resolution grid and a corresponding value of predicted projection data on the resolution grid;
computing a second quantity for each of the plurality of object space voxels, the second quantity corresponding to at least one impulse response combined with contributions from a noise variance, each impulse response corresponding to a reference voxel of unit-intensity at a location in the object space, the second quantity computed using the contributions from the noise variance and at least one of a Kalman filter gain, an approximate Kalman filter gain, a Wiener filter gain, or an approximate Wiener filter gain, wherein computing the second quantity further comprises at least one of:
back-projecting the projection space data for a neighborhood around the reference voxel to produce one or more back-projected outputs and inverting the one or more back-projected outputs combined with the contributions from the noise variance; or
inverting projections of the impulse response modified by a signal-to-noise ratio;

computing an update value for each of the plurality of object space voxels, each update value computed using the corresponding first quantity and the corresponding second quantity;

reconstructing an image representing the object under observation using the update values, and outputting the reconstructed image to an output device, wherein the output device is at least one of the data storage device, another one or more data storage devices, a display device, or a printing device.

32. The storage device according to claim 31, wherein the software, when executed, further causes the one or more processors to:

smooth at least one of the prediction space data and a set of object space voxel data.

* * * * *